United States Patent [19]

Lin et al.

[11] Patent Number: 4,466,927

[45] Date of Patent: Aug. 21, 1984

[54] METHOD FOR THE PREPARATION OF 2-(TRIFLUOROMETHYL)PHENYL CARBAMIC FLUORIDE

[75] Inventors: Henry C. Lin; Byron R. Cotter, both of Grand Island, N.Y.

[73] Assignee: Occidental Chemical Corporation, Niagara Falls, N.Y.

[21] Appl. No.: 504,636

[22] Filed: Jun. 15, 1983

[51] Int. Cl.$^3$ .............................................. C07C 125/03
[52] U.S. Cl. .............................. 260/544 C; 260/544 F
[58] Field of Search ......................... 260/544 C, 544 F

[56] References Cited

FOREIGN PATENT DOCUMENTS 955898  2/1962  United Kingdom .

OTHER PUBLICATIONS

Klauke, E. Angew. Chem. Internat. Ed., vol. 5, (1966), at p. 848.

Primary Examiner—Natalie Trousof
Assistant Examiner—L. Hendriksen
Attorney, Agent, or Firm—James F. Tao; Arthur S. Cookfair

[57] ABSTRACT

A method for the preparation of a 2-(trifluoromethyl)-phenyl carbamic fluoride comprises isomerizing N-(trifluoromethyl)-anthraniloyl fluoride in the presence of hydrogen fluoride to 2-(trifluoromethyl)phenyl carbamic fluoride.

10 Claims, No Drawings

METHOD FOR THE PREPARATION OF 2-(TRIFLUOROMETHYL)PHENYL CARBAMIC FLUORIDE

BACKGROUND OF THE INVENTION AND MATERIAL INFORMATION DISCLOSURE STATEMENT

This invention relates to a method for the preparation of 2-(trifluoromethyl)phenyl carbamic fluorides. The compounds prepared are useful as chemical intermediates for the further preparation of aromatic amines, especially 2-(trifluoromethyl)-benzenamine.

The 2-(trifluoromethyl)-benzamines, also known as o-trifluoromethyl anilines or o-aminobenzotrifluorides, are a known class of compounds having commercial utility as chemical intermediates, particularly as intermediates for the preparation of various dyestuff and pesticides. For example 2-amino-5-chlorobenzotrifluoride is employed commercially as a dye intermediate and is designated as C.I. Azoic Diazo Component 17, according to Colour Index, Chemical No. 37055, Vol. 1–4, 2nd ed. 1956, Suppl. 1963 published by the Society of Dyers and Colourists (U.K.) and The American Association of Textile Chemists and Colorists (U.S.).

The trifluoromethylanilines are disclosed in U.S. Pat. No. 4,243,819, to Henrick et al., as intermediates in the synthesis of amino acid esters having pesticidal properties. Thus, for example, the reference teaches the preparation of the m-phenoxybenzyl ester of N-(2-trifluoromethylphenyl)valine by reaction of 2-trifluoromethylaniline with m-phenoxybenzyl α-bromoisovalerate.

U.S. Pat. No. 4,316,988 to Clinton discloses the use of trifluoromethyl-substituted anilines as intermediates in the synthesis of various diphenylamine products useful as rodenticides, insecticides, and arachnicides.

The utility of the o-aminobenzotrifluorides as chemical intermediates has led to the investigation and development of various methods for the preparation of these compounds.

Forbes et al., Tetrahedron, Vol. 8, 67–72 (1960) prepared o-aminobenzotrifluoride by hydrogenation of 2-nitrotrifluoromethylbenzene at elevated temperatures and pressure in the presence of a Raney nickel catalyst.

German Offenlegungschrift D.E. No. 3,017,542 to Klauke et al. discloses the preparation of o-aminobenzotrifluoride by hydrogenation-hydrogenolysis of 2-amino-5-chlorobenzotrifluoride.

McBee et al., J. Am. Chem. Soc. 73, 3932–34 (1951) disclose the preparation of 4-bromo-2-(trifluoromethyl)-aniline by nitration of 3-bromo-(trifluoromethyl)-benzene followed by reduction of the resultant 2-nitro-5-bromo(trifluoromethyl)-benzene.

Although methods for the preparation of 2-(trifluoromethyl)-benzenamine are known from the prior art, it will be appreciated that the development of improved and more economical processes is desirable. The present invention provides a convenient and economical method for the preparation of 2-(trifluoromethyl)-phenyl carbamic fluorides, which, in turn, have been found particularly useful as an intermediate for the preparation of aminobenzotrifluorides and hydrofluoride salts thereof.

The preparation of phenyl carbamic acid fluorides from aromatic isocyanates is known. Buckley et al. J. Chem. Soc. 864 (1945) disclose the preparation of phenyl carbamic fluorides by reaction of HF with various isocyanates. However, the reference provides no teaching relative to the preparation of phenyl carbamic fluorides bearing a fluoroalkyl side chain.

British Pat. No. 955,898 (1964) to Farbenfabriken Bayer Aktiengesellschaft discloses the reaction of anhydrous hydrogen fluoride with chloromethylphenyl isocyanates to produce the corresponding fluoromethylphenyl carbamic fluoride, or, upon subsequent heating, the corresponding isocyanate. The British patent further discloses the reaction of hydrogen fluoride with 2-trichloromethyl-4-chlorophenyl isocyanate in chlorobenzene to prepare 2-trifluoromethyl-4-chlorophenyl carbamic acid fluoride. Subsequently, Klauke, Angew. Chem. Interat. Ed. Vol. 5, No. 9, 848, (1966), in contrast to the teachings of British Pat. No. 955,898, stated that when o-trichloromethylphenyl isocyanate undergoes Cl—F exchange in anhydrous hydrogen fluoride, isomerization occurs simultaneously and o-N-(trifluoromethyll)aminobenzoyl fluoride can be isolated, thus implying that o-trifluoromethyl phenyl carbamic fluoride is not produced.

In U.S. Pat. No. 3,829,460 to Buttner and Klauke, assigned to Bayer Aktiengesellschaft, reference is made to the 1966 article and to earlier contradictory teachings and it is disclosed that when hydrogen fluoride is reacted with a trichloromethylphenyl isocyanate wherein the trichloromethyl group is in the 2-position to the isocyanate group, it is only possible to obtain the isomer, 2-N-trifluoromethylaminobenzoyl fluorides.

British Pat. No. 1,164,223 to Klauke et al. teaches the hydrolysis of trifluoromethylphenyl isocyanates with 90–100 percent sulfuric acid to produce the corresponding trifluoromethyl benzenamine (or amine.sulfate) with carbon dioxide as the only byproduct.

The hydrolysis of an NCO group with acid agents, such as concentrated hydrochloric acid or sulphamic acid is known (Houben-Weyl, Methoden der org. Chemie, 4th Edition, Vol. 11/1, page 953).

SUMMARY OF THE INVENTION

It has now been found that 2-(trifluoromethyl)phenyl carbamic fluorides of the formula

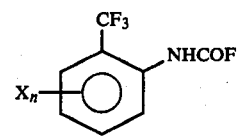

where n is 0 to 2 and X is independently selected from the group fluoro-, chloro-, bromo-, phenyl-, chlorophenyl-, bromophenyl-, and fluorophenyl- can be prepared by isomerizing an N-(trifluoromethyl)-anthraniloyl fluoride of the formula

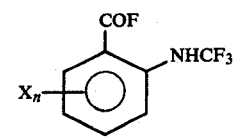

where n and X are as defined above, in the presence of hydrogen fluoride.

The isomerization of N-(trifluoromethyl)-anthraniloyl fluoride to 2-(trifluoromethyl)phenyl carbamic fluoride proceeds readily in the presence of hydrogen fluoride. Preferably, the hydrogen fluoride is present in an amount of about 1.5 to about 25 and most preferably about 4.0 to about 20.0 moles of hydrogen fluoride per mole of N-(trifluoromethyl)-anthraniloyl fluoride. When lesser amounts are employed the isomerization will occur, but the reaction time is much longer. Greater amounts of hydrogen fluoride may be employed, but provide no special advantage.

It is preferred to carry out the isomerization in the liquid phase. The process may be carried out at atmospheric pressure, with the temperature being maintained at or below the boiling point of hydrogen fluoride, or at higher pressures and temperatures under autogenous conditions. Temperatures, for example, in the range of about −10° or less to about 150° Celsius or higher may be employed. Preferably, temperatures in the range of about 20° to about 100° Celsius are employed.

The reaction may be run neat or in the presence of a carrier medium such as methylene chloride. The reaction proceeds smoothly without the need for a catalyst. However, if desired, a catalyst, such as a Lewis acid catalyst, such as antimony pentachloride, may be employed.

The reactants susceptible to isomerization in accordance with this invention include N-(trifluoromethyl)-anthraniloyl fluoride as well as the various derivatives bearing ring-substituents, such as, fluoro-, chloro-, bromo-, phenyl-, chlorophenyl-, fluorophenyl-, or bromophenyl-. The isomerization of N-(trifluoromethyl)-anthraniloyl fluoride to 2-(trifluoromethyl)-phenyl carbamic fluoride is of particular interest due to the utility of the latter as an intermediate for the subsequent preparation of 2-(trifluoromethyl)-benzenamine.

N-(trifluoromethyl)-anthraniloyl fluoride may be conveniently prepared by the reaction of 1-isocyanato-2-(trichloromethyl)-benzene. The reaction may be carried out in the liquid or vapor phase. In the liquid phase the reaction may be carried out at atmospheric pressure, with the temperature being maintained at or below the boiling point of hydrogen fluoride, or at higher pressures and temperatures under autogenous conditions. Typically for a liquid phase reaction, temperatures in the range of about −10° to about 100° Celsius are employed. In a vapor phase reaction the temperature will generally be above the boiling point of the reaction mixture with no practical upper limit. Typically, the vapor phase reaction is run at a temperature of about 250° to about 350° Celsius.

It is preferred to carry out the reaction of the 1-isocyanato-2-(trichloromethyl)-benzene and hydrogen fluoride with at least a slight stoichiometric excess of hydrogen fluoride present at all times. Although there is no theoretical upper limit to the molar ratio of hydrogen fluoride to organic reaction employed, a ratio between about 4:1 and about 25:1 is generally employed. The reaction may be run neat or in the presence of a carrier medium such as methylene chloride.

The N-(trifluoromethyl)-anthraniloyl fluoride reactant may be employed in substantially pure form or, conveniently, as the crude reaction product of hydrogen fluoride and 1-isocyanato-2-(trichloromethyl)-benzene as described in the preceeding paragraph. Thus, in one embodiment, the present invention provides a process for the preparation of 2-(trifluoromethyl)phenyl carbamic fluoride comprising (A) reacting 1-isocyanato-2-(trichloromethyl)-benzene with hydrogen fluoride to form N-(trifluoromethyl)-anthraniloyl fluoride; and (B) isomerizing the N-(trifluoromethyl)-anthraniloyl fluoride in the presence of hydrogen fluoride to form 2-(trifluoromethyl)phenyl carbamic fluoride.

The 2-(trifluoromethyl)phenyl carbamic fluoride resulting from the isomerization step of this invention may be recovered from the crude reaction product in relatively pure form by conventional physical separation means, such as distillation. Alternatively, if the 2-trifluoromethyl)phenyl carbamic fluoride is to be employed as a chemical intermediate for the preparation of 2-(trifluoromethyl)-benzenamine, or the hydrofluoride salt thereof, it may be employed in the crude form, without purification or separation from the reaction mixture. In this instance, the crude 2-(trifluoromethyl)phenyl carbamic fluoride product of the isomerization step is further reacted with hydrogen fluoride to form the hydrofluoride salt or complex of 2-(trifluoromethyl)-benzenamine. A detailed description of the use of 2-(trifluoromethyl)phenyl carbamic fluoride in the further preparation of benzenamines and complexes thereof is disclosed in the commonly assigned application of Lin et al. entitled "Method for the Preparation of Benzenamines" and concurrently filed herewith.

The following specific examples are provided to further illustrate this invention and the manner in which it may be carried out. It will be understood, however, that the specific details given in the examples have been chosen for purpose of illustration and are not to be construed as limitations on the invention. In the examples, unless otherwise indicated, all parts and percentages are by weight and all temperatures are in degrees Celsius.

EXAMPLES 1–5

Isomerization of N(trifluoromethyl)-anthraniloyl fluoride to 2-(trifluoromethyl)phenyl carbamic fluoride

Example 1

Three parts of N-(trifluoromethyl)-anthraniloyl fluoride was charged to a polytetrafluoroethylene reactor. The reactor was maintained at 0° C. while three parts of liquid hydrogen fluoride was added. The reactor was then sealed and the temperature was increased to about 25° C. and maintained thereat, with stirring for about 24 hours. The reactor was opened to atmospheric pressure. Analysis of the liquid reaction product by F-19 nuclear magnetic resonance techniques indicated 7.7% of the starting anthraniloyl fluoride; 20.8% of 2-(trifluoromethyl)benzenamine.hydrofluoride; and 71.5% of 2-(trifluoromethyl)phenyl carbamic fluoride.

Examples 2–5

The procedure of Example 1 was repeated except that various catalysts were incorporated and the molar proportion of hydrogen fluoride and N-(trifluoromethyl)anthraniloyl fluoride reactants was varied with the results as shown in Table I, below. The analysis of the liquid reaction product, in each instance indicated the major component as 2-(trifluoromethyl)phenyl carbamic fluoride (Compound I) with minor proportions of 2-(trifluoromethyl)-benzamine-hydrofluoride (Compound II) and N-(trifluoromethyl)anthraniloyl fluoride starting material.

TABLE I

| Example | Mole Ratio HF:Organic[1] | Catalyst/Parts | Starting Material | Product Composition (%) Compound I[3] | Compound II[4] |
|---|---|---|---|---|---|
| 2 | 15.6 | None | 1.7 | 87.0 | 11.3 |
| 3 | 9.2 | SbCl$_5$/5 parts | 18.7 | 78.3 | 3.4 |
| 4 | 10.3 | FSO$_3$H/11 parts | 16.1 | 73.6 | 10.3 |
| 5 | 13.7 | HCl[2] | 7.4 | 79.6 | 13.0 |

[1]Mole Ratio of HF:N—(trifluoromethyl)-anthraniloyl fluoride
[2]HF used was saturated with HCl
[3]2-(trifluoromethyl)phenyl carbamic fluoride
[4]2-(trifluoromethyl)benzenamine hydrofluoride

EXAMPLES 6–13

Preparation of N-(trifluoromethyl)-anthraniloyl fluoride

Example 6

Anhydrous hydrogen fluoride and 1-isocyanato-2-(trichloromethyl)-benzene were fed at rates of 24 parts per hour and 3 parts per hour, respectively, (mol ratio of HF:organic reactant=94.66) into a vapor phase reactor maintained at about 275° C. The product gases were cooled, condensed and collected. Analysis, of the reaction product, using F-19 nuclear magnetic resonance techniques, indicated an essentially 100% conversion of the organic reactant to N-(trifluoromethyl)-anthraniloyl fluoride.

Examples 7–13

The procedure of Example 1 was repeated except that the temperature of the reactor was varied and the flow rates of reactants were varied to provide molar ratios as shown in the table below.

TABLE II

| Example | Temperature | Molar Ratio[1] | Conversions[2] % |
|---|---|---|---|
| 7 | 300 | 21.29 | 100 |
| 8 | 300 | 94.60 | 100 |
| 9 | 300 | 48.76 | 96.1 |
| 10 | 275 | 35.48 | 96.2 |
| 11 | 275 | 65.04 | 100 |
| 12 | 250 | 94.62 | 100 |
| 13 | 250 | 26.61 | 97.0 |

[1]Molar Ratio of HF:1-isocyanato-2-(trichloromethyl)-benzene
[2]Percent conversion of 1-isocyanato-2-(trichloromethyl)-benzene to N—(trifluoromethyl)-anthraniloyl fluoride

EXAMPLES 14–19

Preparation of 2-(trifluoromethyl)benzenamine from 2-(trifluoromethyl)phenyl carbamic fluoride

Example 14

Three hundred and two parts of 2-(trifluoromethyl)-phenyl carbamic fluoride was charged to a polytetrafluoroethylene reaction vessel and maintained at 0° C. while 420 parts of liquid hydrogen fluoride was added. The reaction vessel was then sealed and the temperature was increased to about 20° C. and maintained thereat, with agitation, for about 16 hours. The reaction was then opened to atmospheric pressure. Analysis of the organic liquid reaction product by gas chromatographic techniques indicated 54.6% 2-(trifluoromethyl)benzenamine.hydrofluoride, and 45.4% of 2-(trifluoromethyl)phenyl carbamic fluoride starting material.

Example 15

2-(Trifluoromethyl)phenyl carbamic fluoride was prepared in situ by the reaction of 187 parts of 1-isocyanato-2-(trifluoromethyl)benzene and 336 parts of hydrogen fluoride at 0° C. Eighteen parts of water was added to the 2-(trifluoromethyl)phenyl carbamic fluoride reaction product and the temperature was increased to about 60° C. The temperature was maintained thereat while hydrogen fluoride was continually refluxed and returned to the reaction mixture. After 24 hours, analysis of the liquid reaction mixture, using gas chromatographic techniques, indicated that the organic reaction product contained 99 percent 2-(trifluoromethyl)benzenamine and 1.0 percent 2-(trifluoromethyl)-phenyl carbamic fluoride.

Examples 16–19

The procedure of Example 15 was repeated except that conditions were varied as shown, with the results as set forth in Table III, below.

TABLE III

| Example | Temperature (°C.) | Pressure Conditions | HF (Parts) | H$_2$O (Parts) | Organic Product Composition (%) 2-(trifluoromethyl) benzenamine | 2-(trifluoromethyl) phenyl carbamic fluoride |
|---|---|---|---|---|---|---|
| 15 | 60 | Atmospheric[1] | 336 | 18 | 99 | 1 |
| 16 | 25 | Atmospheric[1] | 355 | 18 | 63.3 | 36.7 |
| 17 | 25 | Autogenous | 338 | 18 | 54.9 | 45.1 |
| 18 | 60 | Atmospheric[1] | 355 | 0 | 49.9 | 50.1 |
| 19 | 25 | Autogenous | 394 | 0 | 22.2 | 77.1 |

[1]HF Reflux Conditions

What is claimed:
1. A method for the preparation of a 2-(trifluoromethyl)phenyl carbamic fluoride which comprises isomerizing an N-(trifluoromethyl)-anthraniloyl fluoride of the formula

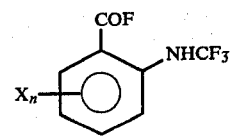

wherein n is 0 to 2 and X is independently selected from the group, fluoro-, chloro-, bromo-, phenyl-, chlorophenyl-, fluorophenyl-, and bromophenyl-, in the presence of hydrogen fluoride to form a 2-(trifluoromethyl)phenyl carbamic fluoride of the formula

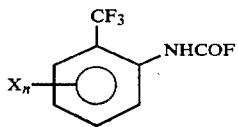

where n and X are as defined above.

2. A method according to claim 1 wherein said isomerization is carried out at a temperature of about −10° to about 150° Celsius.

3. A method according to claim 1 wherein the molar ratio of hydrogen fluoride:N-(trifluoromethyl)-anthraniloyl fluoride is about 1.5:1 to about 25:1.

4. A method according to claim 1 which comprises isomerizing N-(trifluoromethyl)-anthraniloyl fluoride, in the presence of hydrogen fluoride to form 2-(trifluoromethyl)phenyl carbamic fluoride.

5. A method according to claim 4 wherein the molar ratio of hydrogen fluoride:N-(trifluoromethyl)-anthraniloyl fluoride is about 1.5:1 to about 25:1.

6. A method according to claim 5 carried out at about 0° to about 150° Celsius.

7. A method according to claim 6 carried out at autogenous pressure.

8. A method according to claim 4 wherein said N-(trifluoromethyl)-anthraniloyl fluoride is prepared by reaction of 1-isocyanato-2-(trichloromethyl)-benzene with hydrogen fluoride.

9. A method according to claim 8 for the preparation of 2-(trifluoromethyl)phenyl carbamic fluoride which comprises
    (A) reacting 1-isocyanato-2-(trichloromethyl)-benzene with excess hydrogen fluoride to form N-(trifluoromethyl)-anthraniloyl fluoride;
    (B) isomerizing the N-(trifluoromethyl)-anthraniloyl fluoride in the presence of about 1.5 to about 25.0 moles of hydrogen fluoride per mole of N-(trifluoromethyl)-anthraniloyl fluoride at a temperature of between about −10° and about 150° Celsius to form 2-(trifluoromethyl)phenyl carbamic fluoride.

10. A method according to claim 8 wherein the N-(trifluoromethyl)-anthraniloyl fluoride is isomerized in the presence of about 4.0 to about 20.0 moles of hydrogen fluoride per mole of N-(trifluoromethyl)-anthraniloyl fluoride at a temperature of about 20° to about 100° Celsius.

* * * * *